US006325905B1

(12) United States Patent
Matsui et al.

(10) Patent No.: US 6,325,905 B1
(45) Date of Patent: Dec. 4, 2001

(54) SOLID ELECTROLYTE TYPE CARBON DIOXIDE GAS SENSOR ELEMENT

(75) Inventors: Mitsuhiko Matsui; Hirotoshi Ikeya, both of Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 09/492,386

(22) Filed: Jan. 27, 2000

(51) Int. Cl.[7] .................................................. G01N 27/407
(52) U.S. Cl. ............................................ 204/424; 204/426
(58) Field of Search ..................................... 204/421–429

(56) References Cited

U.S. PATENT DOCUMENTS 5,194,134 * 3/1993 Futata et al. ........................ 204/426
5,413,691 * 5/1995 Kaneyasu et al. ................... 204/426

FOREIGN PATENT DOCUMENTS

A580021    3/1993   (JP) .

* cited by examiner

Primary Examiner—T. Tung
(74) Attorney, Agent, or Firm—Birch, Stewart, Kolasch & Birch, LLP (57) ABSTRACT

A solid electrolyte type carbon dioxide gas sensor element has a solid electrolyte layer, a work electrode layer formed on one side of the solid electrolyte layer and containing an electron conducting material and an auxiliary electrode material, and a reference electrode layer formed on the same side or the other side of the solid electrolyte layer and containing an electron conducting material.

The work electrode layer further contains a rare earth metal oxide or at least part of the auxiliary electrode material of the work electrode layer is a rare metal oxide carbonate.

12 Claims, 1 Drawing Sheet

FIG. 1

SOLID ELECTROLYTE TYPE CARBON DIOXIDE GAS SENSOR ELEMENT

DETAILED DESCRIPTION OF THE INVENTION

The present invention relates to a solid electrolyte-use gas sensor element which is incorporated in air cleaner system or environmental instrumentation system to measure the concentration of carbon dioxide gas contained in an atmosphere. More specifically, it relates to a solid electrolyte type carbon dioxide gas sensor element which has attained the improvement of stability in a high-humidity environment and a reduction in the stabilization time of electromotive force in particular.

In recent years, along with a growing interest in environmental problems, monitoring sensors for controlling the concentration of carbon dioxide gas discharged into the atmosphere have been attracting much attention. Out of the sensors, a solid electrolyte type carbon dioxide gas sensor element making use of a change in the electromotive force of a solid electrolyte is small in size, simple in structure and inexpensive. Therefore, the implementation of this solid electrolyte type carbon dioxide gas sensor element has been strongly desired.

The solid electrolyte type carbon dioxide gas sensor element whose implementation is now under study generally comprises a solid electrolyte layer which is an ionic conductor, a work electrode layer which contains an electron conducting material and an auxiliary electrode material, a reference electrode layer containing an electron conducting material and a heater for heating these layers.

This sensor element is generally heated at a fixed temperature of 100 to 600° C. to start operation and generates fixed electromotive force between the work electrode layer and the reference electrode layer through the solid electrolyte layer according to the concentration of carbon dioxide gas when it is left in an atmosphere containing carbon dioxide gas. When the concentration of carbon dioxide gas contained in an atmosphere where the sensor element is left changes, a dissociation equilibrium reaction between the auxiliary electrode material contained in the work electrode layer and carbon dioxide gas proceeds until equilibrium is reached and the concentration of movable ions in the solid electrolyte layer changes in the vicinity of the work electrode layer.

Since this concentration change appears as a change in electromotive force, it is possible to know the concentration of carbon dioxide gas by measuring electromotive force at that time by a voltmeter and using a prepared analytical curve showing the correlation between electromotive force and the concentration of carbon dioxide gas.

The solid electrolyte layer of this carbon dioxide gas sensor is formed of a cation conductor such as NASICON ($Na_{1+A}Zr_2Si_AP_{3-A}O_{12}$, provided that $0 \leq A \leq 3$) a complex oxide containing lithium oxide such as $Li_2SiO_3$, $LiCoO_2$ and $Li_2ZrSi_6O_{15}$, or $\beta$-$Al_2O_3$.

The electron conducting material contained in the work electrode layer is required to detect electromotive force and selected from previous metal materials having excellent heat resistance and oxidation resistance, such as gold and platinum.

The auxiliary electrode material contained in the work electrode layer can cause an equilibrium reaction between it and carbon dioxide gas in an atmosphere containing carbon dioxide gas and is selected from alkali metal carbonates and alkali earth metal carbonates which have dissociation equilibrium with carbon dioxide gas.

Further, the electron conducting material contained in the reference electrode layer is identical to the electron conductive layer contained in the work electrode layer.

The solid electrolyte type carbon dioxide gas sensor which operates with the above constitution has such advantages that it can measure the concentration of carbon dioxide gas contained in an atmosphere very accurately and that it is small in size and can be produced at a low cost. Therefore, it is widely accepted as a sensor element having high general applicability.

JP-A 5-80021 (the term "JP-A" as used herein means an "unexamined published Japanese patent application") discloses a carbon dioxide gas sensor which comprises a detection electrode (work electrode) and a standard electrode (reference electrode) with an ionic conductor therebetween, wherein a coating material for the detection electrode is a solid solution of an alkali earth metal carbonate and an alkali metal carbonate and does not contain alkali metal carbonate crystals.

However, the above solid electrolyte type carbon dioxide gas sensor in which an alkali metal carbonate or alkali earth metal carbonate is used as an auxiliary electrode material has such a problem that when it is left in an atmosphere having a high water concentration such as a high-humidity atmosphere or condensation atmosphere after heating is stopped to suspend the operation of the sensor and then its operation is resumed, electromotive force greatly falls below a value before it is left.

Further, the time interval from the start of operation to the time when electromotive force becomes stable is generally 6 to 8 hours whereas it is 20 to 40 hours when the gas sensor is left in the above atmosphere without being heated.

These problems are factors of preventing the implementation of a solid electrolyte type carbon dioxide gas sensor. Therefore, the development of a solid electrolyte type carbon dioxide gas sensor whose electromotive force does not change even when it is left in an atmosphere having a high water concentration such as high humidity and condensation for a long time without being heated and whose time interval from the start of operation to the time when electromotive force becomes stable is short has been desired.

It is therefore an object of the present invention to provide a solid electrolyte type carbon dioxide gas sensor element which comprises a work electrode layer having novel composition.

It is another object of the present invention to provide a solid electrolyte type carbon dioxide gas sensor element whose a value of electromotive force remains unchanged even when it is left in an atmosphere having a high water concentration such as high humidity and condensation without being heated and whose time interval from the start of operation to the time when electromotive force becomes stable is less than 2 hours.

Other objects and advantages of the present invention will become apparent from the following description.

According to the present invention, firstly, the above objects and advantages of the present invention are attained by a solid electrolyte type carbon dioxide gas sensor element (may be referred to as "first carbon dioxide gas sensor element of the present invention" hereinafter) which comprises a solid electrolyte layer, a work electrode layer formed on one side of the solid electrolyte layer and containing an electron conducting material and an auxiliary electrode material, and a reference electrode layer formed on the same side or the other side of the solid electrolyte layer and containing an electron conducting material, wherein the work electrode layer further containing a rare earth metal oxide.

Secondly, the above objects and advantages of the present invention are attained by a solid electrolyte type carbon dioxide gas sensor element (may be referred to as "second carbon dioxide gas sensor element of the present invention" hereinafter) which comprises a solid electrolyte layer, a work electrode layer formed on one side of the solid electrolyte layer and containing an electron conducting material and an auxiliary electrode material, and a reference electrode layer formed on the same side or the other side of the solid electrolyte layer and containing an electron conducting material, wherein at least part of the auxiliary electrode material of the work electrode layer is a rare earth metal oxide carbonate.

The constitution of the first carbon dioxide gas sensor element of the present invention will be described in detail hereinunder.

In the present invention, it is important that the work electrode layer should contain a rare earth metal oxide. If the work electrode layer does not contain a rare earth metal oxide, when it is left in a high-humidity environment, the value of electromotive force becomes much smaller than a value before it is left and the time interval from the start of operation to the time when electromotive force is stabilized becomes long.

Illustrative examples of the rare earth metal oxide include rare earth metal oxides represented by general formulas $R^1O$, $R^2O_2$ and $R^3{}_2O_3$ ($R^1$, $R^2$ and $R^3$ are divalent, tetravalent and trivalent rare earth metal elements, preferably Sc, Y and lanthanoids having atomic numbers 57 to 71 such as La, Ce, Pr, Nd and Pm). The rare earth metal oxide may be a composite oxide. Illustrative examples of the composite oxide include composite oxides represented by general formulas $R^4MO_2$ and $R^5MO_3$ ($R^4$ and $R^5$ are rare earth metal elements and M is a general metal element encompassing rare earth metal elements, such as Al, Sb, Co, Cr, Cu, Dy, Fe, Ho, Li, Mn, Ni or In). When M is a rare earth metal element, it cannot be the same rare earth metal element as $R^4$ or $R^5$ and the total number of charges of $R^4$ and M is 4 and the total number of charges of $R^5$ and M is 6.

Out of the rare earth metal oxides represented by the above general formulas, rare earth metal oxides containing lanthanoids as rare earth elements are preferred because the time interval from the start of operation of a solid electrolyte type carbon dioxide gas sensor in a high-humidity environment to the time when electromotive force is stabilized becomes short, and rare earth metal oxides containing La and Nd as rare earth elements are particularly preferred.

Out of the rare earth metal oxides, rare earth metal oxides represented by $R^2O_2$ and $R^3{}_2O_3$ are preferred because the time interval from the start of operation to the time when electromotive force is stabilized in a high-humidity environment becomes short.

The content of the rare earth metal oxide in the work electrode layer is not particularly limited but is preferably 0.5 to 80 wt %, particularly preferably 1 to 60 wt % based on 100 wt % of the total weight of the work electrode.

In the present invention, the auxiliary electrode material contained in the work electrode layer is a substance which can cause an equilibrium reaction between it and carbon dioxide gas in an atmosphere containing carbon dioxide gas, and known materials may be used without restriction. Preferred examples of the auxiliary electrode material include alkali metal carbonates, alkali earth metal carbonates and rare earth metal oxide carbonates. They may be used alone or in combination of two or more. Out of the alkali metal carbonates, sodium carbonate and lithium carbonate are preferred. Out of the alkali earth metal carbonates, calcium carbonate and magnesium carbonate are preferred. The rare earth metal oxide carbonates are the same as those which will be enumerated for the second carbon dioxide gas sensor element hereinafter.

A combination of a rare earth metal oxide and an auxiliary electrode material is not particularly limited but a combination of a rare earth metal oxide containing a lanthanoid as a rare earth element and an alkali metal carbonate or rare earth metal oxide carbonate is preferred because the time interval from the start of operation in a high-humidity environment to the time when electromotive force is stabilized becomes short. A combination of lanthanum oxide or neodymium oxide and sodium carbonate or lithium carbonate is particularly preferred.

The content of the auxiliary electrode material in the work electrode layer is not particularly limited but is preferably 1 to 70 wt %, particularly preferably 3 to 50 wt % based on 100 wt % of the total weight of the work electrode because the electromotive force of the sensor element can be easily output stably.

In the present invention, the electron conducting material contained in the work electrode layer is required to output the electromotive force of the sensor element like the electron conducting material contained in the reference electrode layer which will be described hereinafter, and known materials maybe used without restriction. For example, precious metal elements such as platinum, gold, palladium, silver, alloys thereof and mixtures of two or more of the above precious metal elements may be used. Platinum, gold, mixtures and alloys thereof are preferred because they have excellent corrosion resistance.

The content of the electron conducting material in the work electrode layer is not particularly limited but is preferably 10 to 95 wt %, particularly preferably 25 to 90 wt % based on 100 wt % of the total weight of the work electrode.

In the present invention, the structure of the work electrode layer containing an electron conducting material, an auxiliary electrode material and a rare earth metal oxide is not particularly limited. Typical examples of the structure include a structure that layers of an electron conducting material, auxiliary electrode material and rare earth metal oxide are formed on the surface of the solid electrolyte layer, a structure that an auxiliary electrode material and a rare earth metal oxide are dispersed in the electron conducting material of the work electrode layer, and a structure that part or all of a layer of a mixture of an auxiliary electrode material and a rare earth metal oxide formed on the surface of the solid electrolyte layer is covered with an electron conducting material. The structure that an auxiliary electrode material and a rare earth metal oxide are dispersed in an electron conducting material is preferred because this makes it easy to form the work electrode layer.

As means of forming the above work electrode layer, known methods may be used without restriction. For example, advantageously employed are a method in which an electron conducting material, auxiliary electrode material and rare earth metal oxide are kneaded with a solvent and a binder independently or after they are mixed to prepare paste and the paste is applied to the surface of the solid electrolyte by screen printing or the like and baked, and a method in which films of an electron conducting material, auxiliary electrode material and rare earth metal oxide are formed by a thin film forming technique such as sputtering or vapor deposition.

The thickness of the work electrode layer is not particularly limited but is generally in the range of 0.001 to 0.03 mm.

In the present invention, the electron conducting material contained in the reference electrode layer is required to output the electromotive force of the sensor element like the electron conducting material contained in the above-described work electrode layer, and known materials may be used without restriction. For example, precious metal elements such as platinum, gold, palladium, silver, alloys thereof and mixtures of two or more of the above precious metal elements may be used. Platinum, gold, mixtures and alloys thereof are preferred because they have excellent corrosion resistance.

As means of forming the above reference electrode layer, known methods may be used without restriction. For example, the above methods described as the means of forming the work electrode layer may be employed.

The thickness of the reference electrode layer is not particularly limited but is generally in the range of 0.001 to 0.03 mm.

In the present invention, the arrangement of the above work electrode layer and reference electrode layer is not particularly limited if the work electrode layer and the reference electrode layer are in contact with the solid electrolyte layer. For example, the work electrode layer is formed on one side of the solid electrolyte layer and the reference electrode layer is formed on the other side of the solid electrolyte layer, or both the work electrode layer and the reference electrode layer are formed on one side of the solid electrolyte layer at a predetermined interval.

In the present invention, known solid electrolytes may be used in the solid electrolyte layer without restriction. For example, NASICON, $\beta$-$Al_2O_3$, and a complex oxide containing lithium oxide such as $Li_2CoO_2$, $LiCoO_2$ and $ZrSi_6O_{15}$, described above may be used.

As means of forming the solid electrolyte layer, known methods may be used without restriction. Typical forming methods include one in which raw materials for synthesizing a solid electrolyte are baked, molded and heated, one in which raw materials for synthesizing a solid electrolyte are molded and sintered, and one in which raw materials for synthesizing a solid electrolyte are kneaded with a solvent and a binder to prepare paste and the paste is printed on a ceramic or glass substrate by screen printing or the like and baked.

The thickness of the solid electrolyte layer is not particularly limited but is generally in the range of 0.02 to 2.0 mm.

The solid electrolyte type carbon dioxide gas sensor element is generally heated at a fixed temperature of 100 to 600° C. to cause a dissociation equilibrium reaction between the auxiliary electrode material and carbon dioxide gas when in use. As means of heating the sensor element, an external heat source may be used to heat the sensor element, or a ceramic or glass substrate incorporating a heater may be connected to the sensor element and DC or AC is applied to the heater for heating. The installation position of the heater connected to the sensor element is not particularly limited if it is located at a position where it does not interfere with the operation of the sensor element, for example, a position on the reference electrode layer.

A description is subsequently given of the second carbon dioxide gas sensor element of the present invention.

The second carbon dioxide gas sensor element differs from the first carbon dioxide gas sensor element in that a rare earth metal oxide does not always have to be used based on the condition that a rare earth metal oxide carbonate is used as at least part of the auxiliary electrode material of the work electrode layer.

As for what is not described of the second carbon dioxide gas sensor element, it should be understood that the above description of the first carbon dioxide gas sensor element can be applied.

The auxiliary electrode material can cause an equilibrium reaction between it and carbon dioxide gas in an atmosphere containing carbon dioxide gas. In the present invention, it is important that the auxiliary electrode material should contain a rare earth metal oxide carbonate. If the auxiliary electrode material does not contain a rare earth metal oxide carbonate, when it is left in a high-humidity environment, the value of electromotive force becomes much smaller than a value before it is left and the time interval from the start of operation to the time when electromotive force is stabilized becomes long.

Illustrative examples of the rare earth metal oxide carbonate include oxide carbonates represented by the general formulas $R^3_2O_2CO_3$ and $R^3_2O(CO_3)_2$, and hydrates thereof represented by the general formulas $(R^3_2O(CO_3)_2 \cdot xH_2O$ (x is any integer larger than 0)) and $R_AO_L(CO_3)_M(OH)_T$ (A, L, M and T are any integers). R and $R^3$ are rare earth elements such as La, Ce, Pr, Nd, Yb, Sm, Eu, Gd, Dy and Tm.

Out of the rare earth metal oxide carbonates represented by the above general formulas, oxide carbonates represented by $R^3_2O_2CO_3$ and $R^3_2O(CO_3)_2$ are preferred because the time interval from the start of operation of the solid electrolyte type carbon dioxide gas sensor element to the time when electromotive force is stabilized becomes short, and an oxide carbonate represented by $R^3_2O_2CO_3$ is particularly preferred.

Out of the rare earth metal oxide carbonates, oxide carbonates of which rare earth element is La or Nd are particularly preferred because the time interval from the start of operation to the time when electromotive force is stabilized in a high-humidity environment becomes short.

In the present invention, the auxiliary electrode material may contain a rare earth metal oxide carbonate, or the auxiliary electrode material may consist of only a rare earth metal oxide carbonate. To prevent a change in the value of electromotive force after the sensor element is left in a high-humidity environment, the rare earth metal oxide carbonate is preferably contained in the auxiliary electrode material in an amount of 10 wt % or more, particularly preferably 15 wt % or more.

When the auxiliary electrode material contains a compound other than rare earth metal oxide carbonates as another auxiliary electrode material, known auxiliary electrode materials such as alkali metal carbonates and alkali earth metal carbonates, and mixtures and solid solutions thereof may be used as the another auxiliary electrode material without restriction.

In order to reduce the time interval from the start of operation to the time when electromotive force is stabilized in a high-humidity environment, an alkali metal carbonate, particularly $Li_2CO_3$ or $Na_2CO_3$ is preferably used as the another auxiliary electrode material. The content of the alkali metal carbonate in the auxiliary electrode material is not particularly limited but is preferably 0.5 to 3 times the weight of the rare earth metal oxide carbonate.

As means of producing the auxiliary electrode material containing a rare earth metal oxide carbonate, known methods may be used without restriction. Typical production methods include (1) one in which a rare earth metal carbonate is heated at 400 to 900° C. in the atmosphere, (2) one in which a rare earth metal carbonate is heated at 400 to 900° C. in a carbon dioxide atmosphere, (3) one in which a rare earth metal carbonate and another auxiliary electrode material are mixed together and heated at 400 to 900° C. in the atmosphere, (4) one in which a rare earth metal carbonate and another auxiliary electrode material are mixed together and heated at 400 to 900° C. in a carbon dioxide atmosphere, and (5) one in which a rare earth metal oxide carbonate and another auxiliary electrode material are mixed together.

A general example of the above production method (1) will be described hereinunder. An auxiliary electrode material containing a rare earth metal oxide carbonate can be obtained by heating a rare earth metal carbonate as a starting material at a temperature range of 400 to 900° C. in the atmosphere. At this point, an auxiliary electrode material containing one of the above rare earth metal oxide carbonates or a mixture of two or more thereof can be obtained by controlling heating temperature and heating time.

Although part of the rare earth metal carbonate may remain as it is, the metal carbonate serves as an auxiliary electrode material and does not cause any problem in the development of the effect of the present invention. The rare earth metal carbonate may be contained as an oxide according to heating conditions but does not cause any problem in the development of the effect of the present invention.

The above production method (2) is the same as the above production method (1) except that a rare earth metal carbonate as a starting material is heated in a carbon dioxide atmosphere.

A general example of the above production method (3) will be described hereinunder. Raw material powders are obtained by mixing a rare earth metal carbonate and another auxiliary electrode material such as an alkali metal carbonate in a ball mill or automatic mortar and heated at 400 to 900° C. in the atmosphere to obtain an auxiliary electrode material containing a rare earth metal oxide carbonate. By controlling heating temperature and heating time at this point, an auxiliary electrode material containing one of the above rare earth metal oxide carbonates or a mixture of two or more thereof can be obtained.

When an alkali metal carbonate is used as the another auxiliary electrode material, a rare earth metal oxide carbonate and an alkali metal carbonate or an alkali metal released from an alkali metal carbonate may form a solid solution or compound according to heating conditions but the solid solution or compound does not cause any problem in the development of the effect of the present invention.

The above production method (4) is the same as the above production method (3) except that powders of a mixture of a rare earth metal carbonate and another auxiliary electrode material such as an alkali metal carbonate are heated in a carbon dioxide atmosphere.

In the above production method (5), an auxiliary electrode material containing a rare earth metal oxide carbonate can be obtained by mixing together the rare earth metal oxide carbonate obtained by the production method (1) or (2) and another auxiliary electrode material such as an alkali metal carbonate in a ball mill or automatic mortar.

Although the ratio of the electron conducting material to the auxiliary electrode material in the work electrode layer is not particularly limited, the auxiliary electrode material is preferably contained in a weight proportion of 5 to 50% based on the work electrode layer because the electromotive force of the sensor element can be easily output stably.

The first and second carbon dioxide gas sensor elements of the present invention are characterized in that the value of electromotive force remains unchanged even when they are left in a condensation or high-humidity atmosphere without being heated for a long time and the time interval from the start of operation to the time when electromotive force is stabilized can be reduced to 2 hours or less. This stabilization time is shorter than the general stabilization time which is 6 to 8 hours.

Therefore, the present invention has great technical significance in that carbon dioxide gas can be measured for a long time in any environment with high reliability in a short period of time.

The following examples are provided for the purpose of further illustrating the present invention but are in no way to be taken as limiting.

EXAMPLES (1) Water Resistance Test

Right after the manufacture of the solid electrolyte type carbon dioxide gas sensor elements of Examples and Comparative Examples, they are placed in a chamber which can control the concentration of carbon dioxide gas, and DC voltage is applied to a heater from a power source to heat the sensor elements at 450° C.

While the temperature of each of the sensor elements is maintained at 450° C., the concentration of carbon dioxide gas in the chamber is controlled to 350 ppm and 1,000 ppm and electromotive force at each of the above concentrations is measured and taken as initial electromotive force. The difference between the value of electromotive force at 350 ppm and the value of electromotive force at 1,000 ppm is obtained and taken as initial sensitivity.

After the measurement of the initial electromotive force and initial sensitivity, the sensor element is taken out from the chamber and placed in a thermostatic chamber maintained at a temperature of 60° C. and a humidity of 90% and left for 7 consecutive days without heating.

After that, the sensor element is taken out from the thermostatic chamber and the electromotive force and sensitivity thereof are measured in the same manner as in the above methods for measuring initial electromotive force and initial sensitivity and taken as electromotive force and sensitivity after the water resistance test.

The difference between electromotive force after the water resistance test and initial electromotive force and the difference between sensitivity after the water resistance test and initial sensitivity are obtained and changes in electromotive force and sensitivity after the sensor element is left in a condensation or high-humidity atmosphere for a long time without heating are observed.

(2) Measurement of Electromotive Force Stabilization Time

The sensor element is placed in a thermostatic chamber maintained at a temperature of 60° C. and a humidity of 90% and left for 7 consecutive days without heating.

After the sensor element is taken out from the thermostatic chamber, it is placed in a chamber whose carbon dioxide gas concentration is maintained at 350 ppm, and DC voltage is applied to a heater from a power source to heat the sensor element at 450° C. The time interval from the start of heating to the time when the value of electromotive force of the sensor element becomes stable at a range of ±4 mV is measured and taken as the stabilization time of the sensor element.

Examples 1 to 21

Figure 1:
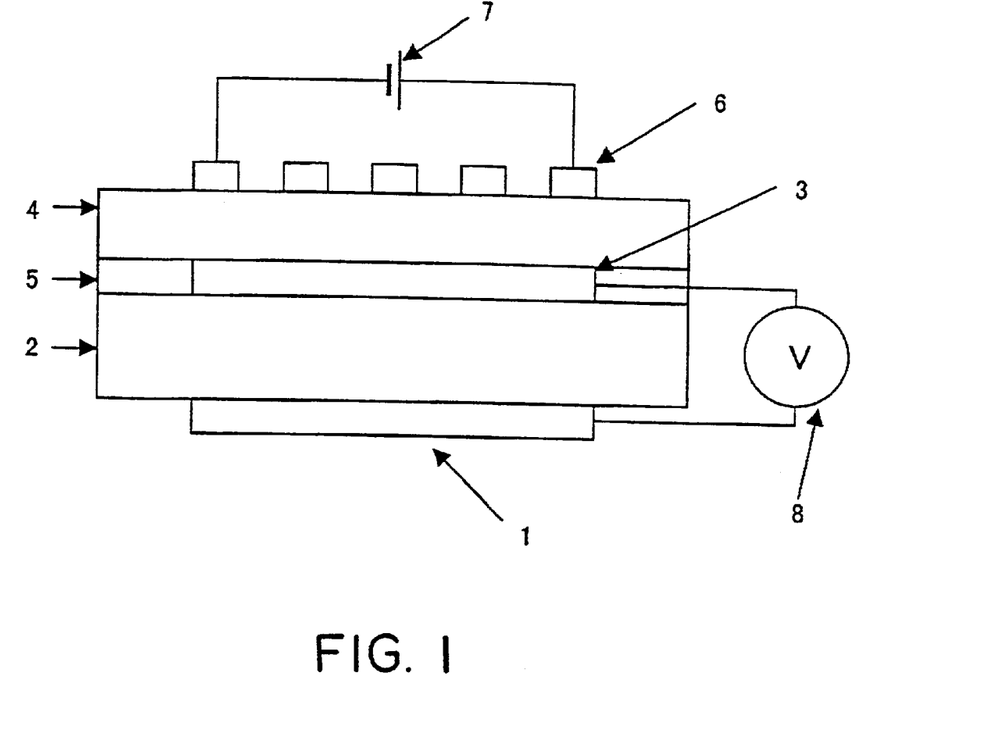
FIG. 1 is a sectional view of a typical example of solid electrolyte type carbon dioxide gas sensor element.

An element having a sectional structure as shown in FIG. 1 was manufactured as a solid electrolyte type carbon dioxide gas sensor. In this solid electrolyte type gas sensor element, a work electrode layer 1 was formed on one side of a solid electrolyte layer 2, a reference electrode layer 3 is formed on the other side of the solid electrolyte layer 2, and a ceramic sheet 4 is bonded to the reference electrode layer 3 by an adhesive 5. Further, a heater 6 is formed on the surface of the ceramic sheet 4 opposite to the surface in contact with the reference electrode layer 3 and supplied with electricity from a power source 7. Lead wires are drawn from the work electrode layer 1 and the reference electrode layer 3 and connected to a voltmeter 8 to measure electromotive force.

Solid electrolyte powders for forming the solid electrolyte layer were obtained by mixing zirconium silicate and sodium phosphate to obtain $Na_3Zr_2SiPO_{12}$ and baking the composition at 1,100° C. in the atmosphere for 6 hours.

The above solid electrolyte powders were molded uniaxially and sintered at 1,200° C. in the atmosphere for 10 hours to obtain a disk-like pellet having a diameter of 3.5 mm and a thickness of 0.4 mm as the solid electrolyte layer 2.

The work electrode layer was formed by kneading gold powders as an electron conducting material, an auxiliary electrode material and a rare earth metal oxide in a ratio shown in Table 1 into a terpineol solution containing 5 wt % of ethyl cellulose to prepare paste, applying this paste to one side of the solid electrolyte layer by screen printing, drying and baking it at 650° C. in the atmosphere for 30 minutes. Thus, the work electrode layer having a thickness of 0.015 mm was obtained.

The reference electrode layer was formed by kneading gold powders as an electron conducting material into a terpineol solution containing 5 wt % of ethyl cellulose to prepare paste, applying the paste to a surface opposite to the work electrode layer of the solid electrolyte layer by screen printing, drying and baking it at 650° C. in the atmosphere for 30 minutes. Thus, the reference electrode having a thickness of 0.015 mm was obtained.

An alumina substrate mounting a platinum heater formed from platinum paste available on the market by screen printing was bonded to the surface devoid of the heater of the above reference electrode layer with a glass adhesive.

A water resistance test and the measurement of electromotive force stabilization time were made on this solid electrolyte carbon dioxide gas element manufactured by the above method. The results are shown in Table 2.

Comparative Examples 1 to 5

All the parts excluding the work electrode layer of each of the solid electrolyte type carbon dioxide gas sensor elements of Comparative Examples 1 to 5 were manufactured in the same manner as in Examples 1 to 21.

The work electrode layers of Comparative Examples 1 to 5 did not contain a rare earth metal oxide. That is, gold powders as an electron conducting material and an auxiliary electrode material shown in Table 1 were kneaded into a terpineol solution containing 5 wt % of ethyl cellulose to prepare paste which was then applied to one side of the solid electrolyte layer by screen printing, dried and baked at 650° C. in the atmosphere for 30 minutes to form the work electrode layers.

A water resistance test and the measurement of electromotive force stabilization time were made on the manufactured sensor elements. The results are shown in Table 2.

TABLE 1

| | constituent ingredients of work electrode layer (wt %) | | | | | | |
|---|---|---|---|---|---|---|---|
| | Au | $La_2O_3$ | $Nd_2O_3$ | $Y_2O_3$ | $CeO_2$ | $Li_2CO_3$ | $Na_2CO_3$ |
| Ex. | | | | | | | |
| 1 | 95 | 1 | | | | 4 | |
| 2 | 74 | 8 | | | | 18 | |
| 3 | 60 | 10 | | | | 30 | |
| 4 | 30 | 20 | | | | 50 | |
| 5 | 40 | 50 | | | | 10 | |
| 6 | 87 | 3 | | | | | 10 |
| 7 | 78 | 10 | | | | | 12 |
| 8 | 45 | 30 | | | | | 25 |
| 9 | 90 | | 2 | | | 8 | |
| 10 | 78 | | 5 | | | 17 | |
| 11 | 75 | | 12 | | | 13 | |
| 12 | 35 | | 25 | | | 40 | |
| 13 | 73 | | 7 | | | | 20 |
| 14 | 25 | | 40 | | | | 35 |
| 15 | 29 | | 56 | | | | 15 |
| 16 | 70 | 5 | 5 | | | 20 | |
| 17 | 74 | 4 | 4 | | | | 18 |
| 18 | 80 | | | 3 | | 17 | |
| 19 | 70 | | | 5 | | | 25 |
| 20 | 80 | | | | 4 | 16 | |
| 21 | 70 | | | | 3 | | 27 |
| C.Ex. | | | | | | | |
| 1 | 75 | | | | | 25 | |
| 2 | 50 | | | | | 50 | |
| 3 | 80 | | | | | | 20 |
| 4 | 60 | | | | | | 40 |
| 5 | 70 | | | | | 15 | 15 |

Ex. = Example
C.Ex. = Comparative Example

TABLE 2

| | initial | | | after water resistance test | | |
|---|---|---|---|---|---|---|
| | electromotive force (mV) | | | electromotive force (mV) | | |
| | 350 ppm | 1000 ppm | sensitivity (mV) | 350 ppm | 1000 ppm | sensitivity (mV) |
| Ex. | | | | | | |
| 1 | 416 | 384 | 32 | 416 | 384 | 32 |
| 2 | 427 | 394 | 33 | 427 | 394 | 33 |
| 3 | 437 | 403 | 34 | 437 | 403 | 34 |
| 4 | 443 | 411 | 32 | 442 | 411 | 31 |
| 5 | 433 | 400 | 33 | 433 | 401 | 32 |
| 6 | 413 | 380 | 33 | 413 | 380 | 33 |
| 7 | 421 | 389 | 32 | 421 | 389 | 32 |
| 8 | 430 | 396 | 34 | 430 | 396 | 34 |
| 9 | 405 | 373 | 32 | 406 | 374 | 32 |
| 10 | 420 | 387 | 33 | 421 | 387 | 34 |
| 11 | 417 | 385 | 32 | 417 | 385 | 32 |
| 12 | 441 | 409 | 32 | 441 | 409 | 32 |
| 13 | 423 | 390 | 33 | 423 | 390 | 33 |
| 14 | 444 | 411 | 33 | 443 | 410 | 33 |
| 15 | 439 | 407 | 32 | 439 | 407 | 32 |
| 16 | 432 | 399 | 33 | 432 | 399 | 33 |
| 17 | 423 | 391 | 32 | 423 | 391 | 32 |
| 18 | 435 | 402 | 33 | 434 | 401 | 33 |
| 19 | 437 | 404 | 33 | 437 | 404 | 33 |
| 20 | 429 | 395 | 34 | 429 | 395 | 34 |
| 21 | 428 | 395 | 33 | 428 | 395 | 33 |
| C. Ex. | | | | | | |
| 1 | 404 | 376 | 28 | 183 | 158 | 25 |
| 2 | 415 | 385 | 30 | 200 | 171 | 29 |
| 3 | 387 | 356 | 31 | 125 | 99 | 26 |
| 4 | 392 | 364 | 28 | 133 | 112 | 21 |
| 5 | 388 | 356 | 32 | 128 | 100 | 28 |

| | difference from initial value | | | |
|---|---|---|---|---|
| | electromotive force (mV) | | | |
| | 350 ppm | 1000 ppm | Sensitivity (mV) | stabilization time (h) |
| Ex. | | | | |
| 1 | 0 | 0 | 0 | |
| 2 | 0 | 0 | 0 | 0.9 |
| 3 | 0 | 0 | 0 | 0.9 |
| 4 | −1 | 0 | −1 | 0.7 |
| 5 | 0 | 1 | −1 | 0.6 |
| 6 | 0 | 0 | 0 | 1.1 |
| 7 | 0 | 0 | 0 | 1 |
| 8 | 0 | 0 | 0 | 0.8 |
| 9 | 1 | 1 | 0 | 1.1 |
| 10 | 1 | 0 | 1 | 0.9 |
| 11 | 0 | 0 | 0 | 0.9 |
| 12 | 0 | 0 | 0 | 0.7 |
| 13 | 0 | 0 | 0 | 1 |
| 14 | −1 | −1 | 0 | 0.8 |
| 15 | 0 | 0 | 0 | 0.6 |
| 16 | 0 | 0 | 0 | 0.7 |
| 17 | 0 | 0 | 0 | 0.7 |
| 18 | −1 | −1 | 0 | 1.9 |
| 19 | 0 | 0 | 0 | 1.9 |
| 20 | 0 | 0 | 0 | 1.5 |
| 21 | 0 | 0 | 0 | 1.6 |
| C. Ex. | | | | |
| 1 | −221 | −218 | −3 | 23.4 |
| 2 | −215 | −214 | −1 | 24.2 |
| 3 | −262 | −257 | −5 | 35.7 |
| 4 | −259 | −252 | −7 | 42.1 |
| 5 | −260 | −256 | −4 | 31.8 |

Examples 22 to 25

Solid electrolyte type carbon dioxide gas sensor elements were manufactured in the same manner as in Examples 1 to 21 except that an auxiliary electrode material containing a rare earth metal oxide carbonate and a work electrode layer were produced as follows.

The auxiliary electrode material containing a rare earth metal oxide carbonate was obtained by baking $La_2(CO_3)_3$ or $Nd_2(CO_3)_3$ which is a carbonate of the rare earth metal at 700° C. in the atmosphere for 30 minutes. The composition measured by X-ray diffraction analysis and fluorescent X-ray analysis of the obtained auxiliary electrode material is shown in Table 3.

The work electrode layer was formed by kneading gold powders as an electron conducting material and an auxiliary electrode material in a ratio shown in Table 4 into a terpineol solution containing 5 wt % of ethyl cellulose to prepare paste, applying the paste to one side of the above solid electrolyte layer by screen printing, drying and baking it at 630° C. in the atmosphere for 30 minutes. Thus, the work electrode layer having a thickness of 0.015 mm was obtained. The results are shown in Table 4.

Examples 26 to 31

Solid electrolyte type carbon dioxide gas sensor elements were manufactured in the same manner as in Example 22 except that an auxiliary electrode material containing a rare earth metal oxide carbonate obtained by mixing together $La_2(CO_3)_3$ or $Nd_2(CO_3)_3$ and $Li_2CO_3$ or $Na_2CO_3$, grinding the resulting mixture in an automatic mortar and baking it at 700° C. in the atmosphere for 30 minutes was used. The composition measured by X-ray diffraction analysis and fluorescent X-ray analysis of the obtained auxiliary electrode material is shown in Table 3.

A water resistance test and the measurement of electromotive force stabilization time were made on the manufactured sensor elements. The results are shown in Table 4.

Example 32

A solid electrolyte type carbon dioxide gas sensor element was manufactured in the same manner as in Example 22 except that an auxiliary electrode material containing a rare earth metal oxide carbonate obtained by mixing together $La_2(CO_3)_3$ and $Nd_2(CO_3)_3$, grinding the resulting mixture in an automatic mortar and baking it at 700° C in the atmosphere for 30 minutes was used. The composition measured by X-ray diffraction analysis and fluorescent X-ray analysis of the obtained auxiliary electrode material is shown in Table 3.

A water resistance test and the measurement of electromotive force stabilization time were made on the manufactured sensor element. The results are shown in Table 4.

Example 33

A solid electrolyte type carbon dioxide gas sensor element was manufactured in the same manner as in Example 22 except that an auxiliary electrode material containing a rare earth metal oxide carbonate obtained by baking $La_2(CO_3)_3$ at 650° C. in the atmosphere for 10 minutes was used. The composition measured by X-ray diffraction analysis and fluorescent X-ray analysis of the obtained auxiliary electrode material is shown in Table 3.

A water resistance test and the measurement of electromotive force stabilization time were made on the manufactured sensor element. The results are shown in Table 4.

Example 34

A solid electrolyte type carbon dioxide gas sensor element was manufactured in the same manner as in Example 22 except that an auxiliary electrode material containing a rare earth metal oxide carbonate obtained by baking $La_2(CO_3)_3$ at 900° C. in the atmosphere for 20 minutes was used. The composition measured by X-ray diffraction analysis and fluorescent X-ray analysis of the obtained auxiliary electrode material is shown in Table 3.

A water resistance test and the measurement of electromotive force stabilization time were made on the manufactured sensor element. The results are shown in Table 4.

Example 35

A solid electrolyte type carbon dioxide gas sensor element was manufactured in the same manner as in Example 22 except that an auxiliary electrode material containing a rare earth metal oxide carbonate obtained by mixing together $La_2(CO_3)_3$ and $Li_2CO_{31}$ grinding the resulting mixture in an automatic mortar and baking it at 650° C. in the atmosphere for 10 minutes was used. The composition measured by X-ray diffraction analysis and fluorescent X-ray analysis of the obtained auxiliary electrode material is shown in Table 3.

A water resistance test and the measurement of electromotive force stabilization time were made on the manufactured sensor element. The results are shown in Table 4.

Example 36

A solid electrolyte type carbon dioxide gas sensor element was manufactured in the same manner as in Example 22 except that an auxiliary electrode material containing a rare earth metal oxide carbonate obtained by mixing together $La_2(CO_3)_3$ and $Li_2CO_3$, grinding the resulting mixture in an automatic mortar and baking it at 900° C. in the atmosphere for 20 minutes was used. The composition measured by X-ray diffraction analysis and fluorescent X-ray analysis of the obtained auxiliary electrode material is shown in Table 3.

A water resistance test and the measurement of electromotive force stabilization time were made on the manufactured sensor element. The results are shown in Table 4.

Comparative Examples 6 to 10

All the parts excluding the work electrode layer of each of the solid electrolyte type carbon dioxide gas sensor elements of Comparative Examples 6 to 10 were manufactured in the same manner as in Examples 22 to 36.

The work electrode layers of Comparative Examples 6 to 10 were formed by kneading gold powders as an electron conducting material and an auxiliary electrode material shown in Table 3 into a terpineol solution containing 5 wt % of ethyl cellulose to prepare paste, applying the paste to one side of the solid electrolyte layer by screen printing, drying and baking it at 650° C. in the atmosphere for 30 minutes.

As for $Li_2CO_3$ and $Na_2CO_3$ contained in Comparative Examples 6 to 10, reagent raw materials were used as they are.

A water resistance test and the measurement of electromotive force stabilization time were made on the manufactured sensor elements. The results are shown in Table 4.

TABLE 3

| | composition of auxiliary electrode material (wt %) | | | | | | composition of work electrode layer (wt %) | |
|---|---|---|---|---|---|---|---|---|
| | rare earth metal oxide carbonate | | others | | | | | auxiliary electrode |
| | $La_2O_2CO_3$ | $Nd_2O_2CO_3$ | $Li_2CO_3$ | $Na_2CO_3$ | $La_2(CO_3)_3$ | $La_2O_3$ | AU | material |
| Ex. | | | | | | | | |
| 22 | 100 | 0 | 0 | 0 | 0 | 0 | 80 | 20 |
| 23 | 100 | 0 | 0 | 0 | 0 | 0 | 50 | 50 |
| 24 | 0 | 100 | 0 | 0 | 0 | 0 | 90 | 10 |
| 25 | 0 | 100 | 0 | 0 | 0 | 0 | 60 | 40 |
| 26 | 50 | 0 | 50 | 0 | 0 | 0 | 80 | 20 |
| 27 | 29 | 0 | 71 | 0 | 0 | 0 | 65 | 35 |
| 28 | 60 | 0 | 0 | 40 | 0 | 0 | 50 | 50 |
| 29 | 0 | 40 | 60 | 0 | 0 | 0 | 50 | 50 |
| 30 | 0 | 63 | 0 | 37 | 0 | 0 | 60 | 40 |
| 31 | 0 | 33 | 0 | 67 | 0 | 0 | 70 | 30 |
| 32 | 50 | 50 | 0 | 0 | 0 | 0 | 70 | 30 |
| 33 | 80 | 0 | 0 | 0 | 20 | 0 | 50 | 50 |
| 34 | 71 | 0 | 0 | 0 | 0 | 29 | 65 | 35 |
| 35 | 57 | 0 | 29 | 0 | 14 | 0 | 65 | 35 |
| 36 | 43 | 0 | 43 | 0 | 0 | 14 | 65 | 35 |
| C. Ex. | | | | | | | | |
| 6 | 0 | 0 | 100 | 0 | 0 | 0 | 75 | 25 |
| 7 | 0 | 0 | 100 | 0 | 0 | 0 | 50 | 50 |
| 8 | 0 | 0 | 0 | 100 | 0 | 0 | 80 | 20 |
| 9 | 0 | 0 | 0 | 1000 | 0 | 0 | 60 | 40 |
| 10 | 0 | 0 | 50 | 50 | 0 | 0 | 70 | 30 |

Ex. = Example   C. Ex. = Comparative Example

TABLE 4

| | initial | | | after water resistance test | | |
|---|---|---|---|---|---|---|
| | electromotive force (mV) | | | electromotive force (mV) | | |
| | 350 ppm | 1000 ppm | sensitivity (mV) | 350 ppm | 1000 ppm | sensitivity (mV) |
| Ex. | | | | | | |
| 22 | 353 | 324 | 29 | 353 | 324 | 29 |
| 23 | 370 | 340 | 30 | 371 | 340 | 31 |
| 24 | 363 | 333 | 30 | 363 | 333 | 30 |
| 25 | 382 | 348 | 34 | 381 | 347 | 34 |
| 26 | 394 | 361 | 33 | 394 | 360 | 34 |
| 27 | 383 | 347 | 36 | 383 | 347 | 36 |
| 28 | 366 | 335 | 31 | 365 | 334 | 31 |
| 29 | 401 | 371 | 30 | 401 | 371 | 30 |
| 30 | 358 | 326 | 32 | 357 | 325 | 32 |
| 31 | 351 | 320 | 31 | 351 | 321 | 30 |
| 32 | 379 | 347 | 32 | 379 | 347 | 32 |
| 33 | 368 | 338 | 30 | 368 | 337 | 31 |
| 34 | 355 | 324 | 31 | 355 | 324 | 31 |
| 35 | 381 | 352 | 29 | 380 | 351 | 29 |
| 36 | 390 | 359 | 31 | 390 | 359 | 31 |
| C. Ex. | | | | | | |
| 6 | 404 | 376 | 28 | 183 | 158 | 25 |
| 7 | 415 | 385 | 30 | 200 | 171 | 29 |
| 8 | 387 | 356 | 31 | 125 | 99 | 26 |
| 9 | 392 | 364 | 28 | 133 | 112 | 21 |
| 10 | 388 | 356 | 32 | 128 | 100 | 28 |

TABLE 4-continued

| | difference from initial value | | | |
|---|---|---|---|---|
| | electromotive force (mV) | | | |
| | 350 ppm | 1000 ppm | Sensitivity (mV) | stabilization time (h) |
| Ex. | | | | |
| 22 | 0 | 0 | 0 | 1.7 |
| 23 | 1 | 0 | 1 | 1.4 |
| 24 | 0 | 0 | 0 | 1.9 |
| 25 | −1 | −1 | 0 | 1.5 |
| 26 | 0 | −1 | 1 | 0.6 |
| 27 | 0 | 0 | 0 | 0.4 |
| 28 | −1 | −1 | 0 | 0.8 |
| 29 | 0 | 0 | 0 | 0.6 |
| 30 | −1 | −1 | 0 | 0.8 |
| 31 | 0 | 1 | −1 | 0.7 |
| 32 | 0 | 0 | 0 | 1.3 |
| 33 | 0 | −1 | 1 | 1.4 |
| 34 | 0 | 0 | 0 | 1.6 |
| 35 | −1 | −1 | 0 | 0.5 |
| 36 | 0 | 0 | 0 | 0.5 |
| C. Ex. | | | | |
| 6 | −221 | −218 | −3 | 23.4 |
| 7 | −215 | −214 | −1 | 24.2 |
| 8 | −262 | −257 | −5 | 35.7 |
| 9 | −259 | −252 | −7 | 42.1 |
| 10 | −260 | −256 | −4 | 31.8 |

What is claimed is:

1. A solid electrolyte carbon dioxide gas sensor element comprising:

a solid electrolyte layer;

a work electrode layer formed on one side of the solid electrolyte layer and containing an electron conducting material and an auxiliary electrode material; and a reference electrode layer formed on the same side or the other side of the solid electrolyte layer and containing an electron conducting material, wherein the work electrode layer further contains a rare earth metal oxide, wherein the rare earth metal oxide of the work electrode layer is at least one member selected from the group consisting of oxides represented by the following formulas: $R^1O$, $R^2O_2$ and $R^3_2O_3$ wherein $R^1$ is a divalent rare earth metal, $R^2$ is a tetravalent rare earth metal and $R^3$ is a trivalent rare earth metal.

2. The carbon dioxide gas sensor element of claim 1, wherein the solid electrolyte layer is formed of a cation conductor selected from the group consisting of a compound represented by the following formula:

$$Na_{1+A}Zr_2Si_AP_{3-A}O_{12}$$

wherein A is a number of 0 to 3, a complex oxide containing lithium oxide, and $\beta\text{-}Al_2O_3$.

3. The carbon dioxide gas sensor element of claim 1, wherein the electron conducting material of the work electrode layer is at least one member selected from the group consisting of gold, platinum and a combination thereof.

4. The carbon dioxide gas sensor element of claim 1, wherein the auxiliary electrode material of the work electrode layer is at least one carbonate selected from the group consisting of alkali metal carbonates, alkali earth metal carbonates and rare earth metal oxide carbonates.

5. The carbon dioxide gas sensor element of claim 1, wherein the rare earth metal oxide is contained in an amount of 0.5 to 80 wt % based on the work electrode layer.

6. The carbon dioxide gas sensor element of claim 1, wherein the electron conducting material of the reference electrode layer is at least one member selected from the group consisting of gold, platinum and a combination thereof.

7. A solid electrolyte carbon dioxide gas sensor element comprising:

a solid electrolyte layer;

a work electrode layer formed on one side of the solid electrolyte layer and containing an electron conducting material and an auxiliary electrode material; and a reference electrode layer formed on the same side or the other side of the solid electrolyte layer and containing an electron conducting material, wherein at least part of the auxiliary electrode material of the work electrode layer is a rare earth metal oxide carbonate represented by the following formula:

$$R^3_2O_2CO_3 \text{ or } R^3_2O(CO_3)_2$$

wherein $R^3$ is a rare earth element.

8. The carbon dioxide gas sensor element of claim 7, wherein the solid electrolyte layer is formed of a cation conductor selected from the group consisting of a compound represented by the following formula:

$$Na_{1+A}Zr_2Si_AP_{3-A}O_{12}$$

wherein A is a number of 0 to 3, a complex oxide containing lithium oxide, and $\beta\text{-}Al_2O_3$.

9. The carbon dioxide gas sensor element of claim 7, wherein the electron conducting material of the work electrode layer is at least one member selected from the group consisting of gold, platinum and a combination thereof.

10. The carbon dioxide gas sensor element of claim 7, wherein the auxiliary electrode material other than rare earth metal oxide carbonates of the work electrode layer is at least one carbonate selected from the group consisting of alkali metal carbonates and alkali earth metal carbonates.

11. The carbon dioxide gas sensor element of claim 7, wherein the work electrode layer contains a rare earth metal oxide carbonate, and at least one carbonate selected from the group consisting of alkali metal carbonates and alkali earth metal carbonates, as auxiliary electrode materials.

12. The carbon dioxide gas sensor element of claim 7, wherein the electron conducting material of the reference electrode layer is at least one member selected from the group consisting of gold, platinum and a combination thereof.

* * * * *